United States Patent [19]

Irikura et al.

[11] Patent Number: 4,777,241

[45] Date of Patent: Oct. 11, 1988

[54] PROTEINACEOUS SUBSTANCE SHOWING ANTITUMOROUS ACTION AND ITS PREPARING METHOD

[75] Inventors: Tsutomu Irikura, Tokyo; Koichi Takagi, Oomiya; Jiro Hosomi, Otone; Satoshi Murayama, Tochigi; Koji Saito, Oyama; Takashi Okazaki, Tochigi, all of Japan

[73] Assignee: Kyorin Pharmaceutical Co., Ltd., Tokyo, Japan

[21] Appl. No.: 885,737

[22] Filed: Jul. 21, 1986

Related U.S. Application Data

[63] Continuation of Ser. No. 767,079, Aug. 20, 1985, abandoned, which is a continuation of Ser. No. 671,200, Nov. 14, 1984, abandoned.

[30] Foreign Application Priority Data

Nov. 21, 1983 [JP] Japan .................................. 58-218985

[51] Int. Cl.$^4$ .......................................... C07K 15/00
[52] U.S. Cl. ................................ 530/350; 530/412; 530/413; 530/415; 530/416; 530/417; 530/825; 435/68
[58] Field of Search ........ 530/380, 412, 413, 415–417, 530/825; 435/68–70

[56] References Cited

U.S. PATENT DOCUMENTS 4,436,656  3/1984  Sasaki et al. .................. 260/112 R
4,481,137  1/1984  Ohnishi et al. ...................... 530/350

FOREIGN PATENT DOCUMENTS 0134247  7/1985  European Pat. Off. .
3227262  3/1983  Fed. Rep. of Germany .

OTHER PUBLICATIONS

Rubin et al., *PNAS*, 82, 1985, p. 6637.
Zacharchuk et al., *PNAS*, 80, 1983, p. 6341.
Toth et al., *Mol. Immunol.* 16, 1979, pp. 671–679.
"Phagocytosis and Cytolysis by a Macrophage Tumour and Its Cloned Cell Line", *Nature* 257, pp. 393–394 (1975), Ralph et al.
Infection and Immunity, vol. 30, No. 2, 1980, pp. Source of Tumoricidal Activity (Tumor-Necrotizing Factor)" *p. 523, Abstract and right-hand col., paragraph 3*.
Chemical Abstracts, vol. 94, No. 11, Mar. 16th, 1981, p. 257, No. 78873x, Columbus, Ohio, U.S.; N. Matthews et al.: "Tumor-Necrosis Factor from the Rabbit, IV., Purification and Chemical Characterization", & Br. J. Cancer 1980, 42(3), 416–22 *Abstract*.
The Journal of Immunology, vol. 125, No. 4, Oct. 1980, pp. 1671–1677, the Williams & Wilkins Co., U.S.; M. R. Ruff et al.: "Purification and Physicochemical Characterization of Rabbit Tumor Necrosis Factor" *p. 1671, Abstract*.

(List continued on next page.)

*Primary Examiner*—John Kight
*Assistant Examiner*—Garnette D. Draper
*Attorney, Agent, or Firm*—Oblon, Fisher, Spivak, McClelland & Maier

[57] ABSTRACT

A proteinaceous substance having the following biochemical characteristics:

(A) a strong cytolytic activity against mouse tumor cells L-929, but not cytotoxic activity for normal cells such as human fetus fibroblasts, human adult skin fibroblasts and chinese hamster fibroblasts (Don, V-79) and therefore a high tumor specificity: and

(B) a strong anti-tumor and immunogenic activity against Meth-A sarcoma. When said substance is injected intravenously to the syngenic BALB/C mice inoculated with Meth-A sarcoma at a quantity of more than 72 units head, not only hemorrhagic necrosis, but also complete degradation is observed. Thereafter, even if it is attempted again to transplant the Meth-A sarcoma cells under the skin of Mice cured completely, successful plantation is not observed because of an acquired immunity:

(C) the substance has no pyrogenetic action after intravenous injection to rabbits:

(D) a molecular weight of 45,000±5,000 (determined by the gel filtration method with Sephacryl S-200): and (E) an isoelectric point pI of 4.8+0.3: and a method for its manufacture.

11 Claims, 4 Drawing Sheets

OTHER PUBLICATIONS

Proc. Natl. Acad. Sci. U.S.A., vol. 80, Sep. 1983, pp. 5397–5401; B. D. Williamson et al.: "Human Tumor Necrosis Factor Produced by Human B-Cell Lines: Synergistic Cytotoxic Interaction with Human Interferon" *p. 5397, Abstract*.

Chemical Abstracts, vol. 96, No. 9, Mar. 1st, 1982, p. 455, No. 67110m, Columbus, Ohio, U.S.; N. Matthews: "Production of an Antitumor Cytotoxin by Human Monocytes", & Immunology 1981, 44(1), 135–42.

PROTEINACEOUS SUBSTANCE SHOWING ANTITUMOROUS ACTION AND ITS PREPARING METHOD

This application is a continuation of application Ser. No. 767,079, filed Aug. 20, 1985, now abandoned, which is a continuation of Ser. No. 671,200, filed Nov. 14, 1984, now abandoned.

DETAILED DESCRIPTION OF THE INVENTION

Field of the Invention

The substance of the present invention is an antitumor-proteinaceous substance that is released into the culture supernatant by cultured cells such as mammalian cultured cells that are able to proliferate without any restriction and to differentiate to macrophage-type cells by a lipopolysaccharide of E. coli. The cells take the form of round-type cells which have phagocytic activity.

Closely related to the invention is a report by Pincus W. B. in 1967 (Fincus W. B., J. Reticuloendothel. Soc. Vol. 4, Page 122–139 (1967)), which described that when purified tuberculin protein was added to the culture liquid or peritoneal cavity macrophages of a normal guinea pig, the macrophages released into the medium a substance having killing activity against mouse tumor cells. Previously, the tumor-killing action of the macrophage had been considered to be caused by direct contact with target cells. Therefore, this report was an important advance which showed that there was a soluble intermediate substance.

Secondly, Meltzer M. S. et al made it clear in 1972 (Meltzer M. S., G. L. Bartlett, J. Natl. Cancer Inst. Vol. 49, Page 1439–1443 (1975)) that when purified tuberculin protein was added to mouse spleen cells activated through BCG sensitization and the cells were cultured, a substance was present in the supernatant liquid. The substance did not act against normal fetal cells and normal fibroblast cells, but did kill L cells specifically. This report was also important since it showed that the substance differs from an indiscriminate cytotoxin (Lymphotoxin) obtained from lymphocytes and it acts specifically against only tumor cells.

Thirdly, Carswell et al made it clear in 1975 (Carswell E. A., L. J. Old et al, Proc. National Academy of Science, U.S.A., Vol. 72, page 3666–3670 (1975)) that when colibacillus toxin LPS was injected intravenously into mice infected with BCG, a substance having L cell killing activity was released into the serum at 2 hours after the injection of LPS. Moreover, this serum did not show toxicity against normal animals and normal cells, but did induce hemorrhagic necrosis or a complete cure after 0.5 ml of this serum was injected into mice bearing Meth-A tumors. Carswell et al named the substance tumor necrosis factor (hereinafter abbreviated as TNF). It was made clear that the molecular weight of TNF is about 150,000.

Since these studies, although many supplementary examinations were performed by investigators such as Mathews N., Ruff M. R., Mannel D. N., Kull F. C. Jr. et al, it has been unclear whether TNF is a pure substance or a mixture of several materials of the same activity.

Since Carswell et al studied TNF, the number of studies on active substances which do not act against normal cells but only act against tumor cells has increased. The direction of study has been divided into four groups, as follows:

1. The first direction of investigation gave attention to finding a less toxic substace than LPS. Lipid A of low toxicity, Pseudomonas aeruginosa killed fungus, and endotoxin obtained by deacetylating LPS in methanol were examined.

2. The second direction gave attention to applying to human cancer therapy mouse and rabbit TNF by the same method as Carswell et al. This idea is based on the fact that interleukin-1 and interleukin-2, which are also lymphokines like TNF, have the property of acting in different species, and there is the possibility of human application of TNF even if it is obtained from other animals. However this method has a drawback in that the extraction should be carried out from whole serum. Therefore, quite different results are found by different investigators, even considering molecular weight alone.

3. This is a method of obtaining the antitumorous active substance from the supernatant liquid of culture cells in vitro. It is the same as 2 (above) in that this substance may be applicable to humans even if it is obtained from animal cells; thus, an active substance originating from human beings is obtainable.

4. This is a method of obtaining an antitumorous active substance by a biotechnology technique wherein, when the antitumorous active substance can be obtained from culture cells, the messenger RNA of the cells is isolated and transformed into colibacillus or yeast. In this method, a peptide chain can be obtained, but there is a possibility of not reaching the immunotolerant state because of the lack of a sugar chain. Therefore, this method remains doubtful.

Now, in the case of the method of obtaining the antitumorous active substance from the supernatant liquid of the culture as described in 3 (above), the growth of the cells obtained from normal animals is slow, and it is difficult to culture them in succession over perdurable generations, so this method is unsuitable for industrial application. There, it is desirable naturally to use tumorous cells which are fast to proliferate. The investigators using these for the first time are Mannel D. N. et al (Mannel D. N., R. N. Moore and S. E. Marzenhagen, Infect. and Immun., Vol. 30, page 523–530 (1980)). They reported that when LPS was added to macrophage-like cells PU5-1.8, and the cells were cultured for 2 hours, the cells released into the medium a substance having heat stability for 30 minutes at 56° C. and a molecular weight of 50,000 to 60,000.

Moreover, in 1983, Williamson B. D. et al (Williamson B. D., E. A. Carswell, B. Y. Rubin, J. S. Prendergastand, L. J. Old, Proc. Natl. Acad. Soc. U.S.A. Vol. 80, page 5397–5401 (1983)) found that human TNF having a molecular weight of about 70,000 was produced from a human B cell tumor transformed by Epstein bar virus. Ohnishi et al (Vienna Intern. Chemotherapy Soc., Preprint PS 12.4: 7-26 (1983)) also reported that human B tumor cells and BALL-1 cells released an antitumorous substance having a molecular weight of about 15,000 when the cells were treated with Sendai virus.

The differences between the substance of the present invention and the substances in the reports indicated above are as follows:

A. Only the histocytes having a phagocytic ability among the reticulosarcoma cells were cloned and used. Among J774.1 cells cloned by Ralph P. et al (Ralph P. and L. Nakoinz, Nature Vol. 257, page 393–394 (1975))

only the circular cells were further cloned and used. Moreover, the human cells in a similar series, U-937 etc., are usable after being submitted to cloning to obtain circular cells having a strong phagocytic ability.

Moreover, Burkitt lymphoma cells transformed with an Epstein bar virus such as Raji, DAUD 1, and RAMOS, can be used after being submitted to cloning. Still further, it is possible to to use hybridomas made with monocytes such as U-937 or J-111 and a B cell tumor, for example, BALL-1, U-704, and the like.

It is a special feature of this invention to use cells without allowing them to differentiate to macrophages with a stimulant.

B. Although the cells assuming the form of monocytes and described in A. are able to differentiate to macrophage-like cells by adding LPS, vegetable lectin and the like, the special feature of the present invention lies in that it is released from cells having a shape before differentiation. Therefore, extraction is easy because of the absence of substances such as LPS which are difficult to separate.

C. The culture cells shown in A. grow vigorously in a medium containing calf fetal serum (doubling times, 24 hours). After being allowed to proliferate sufficiently with this calf fetal serum, the medium is exchanged with nonserum medium and the cells are cultured for several days to collect the supernatant liquid.

The invention has a special feature in that since the cells remaining behind are not damaged, they are utilized again to produce the supernatant liquid of the nonserum medium after they have been transferred to the serum medium. This is extremely advantageous industrially.

D. On the extraction of the proteinaceous substance of the invention from the serum-free medium, bovine albumin and transferrin (which are the main proteins in the medium) can be rapidly removed with Blue Sepharose and DEAE-Sephadex. Moreover, ammonium sulfate does not affect the purification of the substances of the invention because it causes neither polymerization nor association. Therefore, the pure substance can be obtained easily. Even if lysozyme or interleukin-1 are present in the supernatant liquid obtained by the method of the invention, they can be readily removed by the use of gel filtration or ultrafiltration, since they have molecular weights of 14,400 and 15,000.

E. The substance of the invention is injected at random into the skin of mice together with an adjuvant, the mice are sensitized once more, and then their spleen cells are collected.

Then, a hybridoma with a B tumor cell of syngeneic mice is prepared to obtain a monoclonal antibody. If this method utilizes the purification and determination thereof, process control can be accomplished with great ease.

F. The proteinaceous substance obtainable by the method of the invention has a molecular weight of 45,000±5,000 and an isoelectric point of pI 4.8±0.3.

It is stable for heating at 56° C. for 30 minutes. It has different properties from human TNF obtained from human B cells by Williamson B. D. et al since their TNF has a molecular weight of 70,000. Further, it is different from the active substance obtained from BALL-1 by Ohnishi H. et al which has a molecular weight of 15,000. Therefore, the physiochemical values of this substance are different in both cases.

G. The substance of the invention does not have pyrogenic activity, and it causes neither abnormal behavior nor death in rabbits even if injected intravenously in a large quantity.

H. The substance is different in physiological action from Colony stimulating factor (CSF) which has the action of increasing granulocytes. CSF is made by adding a stimulator such as LPS, dextran, zymosan, tuberculin, PMA and the like to the macrophage culture.

I. When PMA or LPS is allowed to react with P 388D1 cells (macrophage-type cultured cells), interleukin-1 is formed in the supernatant liquid of the culture. Since this has a molecular weight of 14,000, has pyrogenic activity, and produces an amyloid-like substance in serum, these properties are evidently different from the proteinaceous substance according to the invention.

Properties approximate to the antitumorous active substances originating from cells known hitherto are as follows:

J. The substance of the invention shows a cell-killing effect on L-929, Meth-A, S-180 and L 1210 of mouse tumor cells in vitro. At the same time, it shows a similar killing effect on human carcinoma (HSC-1, EAC-1 and HeLa).

On the other hand, it shows no killing effect on normal cells such as fetal or adult human skin fibroblasts and V-79 and Don animal cells. That is, its tumor specificity is high.

K. When the diameter of the congenic Meth-A tumor reached 5 to 6 mm in BALB/c mice, the mice were injected intraveneously with the compound of the invention once at 72 units. As a result, it was observed not only that the tumor underwent hemorrhagic necrosis, but also infiltration of lymphocytes. Afterward, the tumor dropped out after about 7 days and 84% of the animals were completely cured. The rate of complete cure is high compared with 25% observed by Carswell et al.

When 10 cells of the same tumoar are implanted again under the skin of completely cured mice, the tumor does not survive. This result shows formation of immunity to the tumor. Hereinafter, the proteinaceous substance in accordance with the invention is called antitumorous factor (hereinafter abbreviated as ATF).

L. ATF is an acidic protein having a molecular weight of 45,000±5,000 and it may involve some sugar. It is sensitive to trypsin, but stable to heating at 56° C. for 30 minutes. It is not inactivated with RNAase or with galactosidase.

M. The amino acid content of ATF was determined by subjecting ATF to total hydrolysis in six normal HCl for 20 hours. The amino acid components were then determined using an automatic amino acid analyzer (Hitachi, type 835). The following amino acid content was found:

TABLE

| Amino Acid | Number of Residues | Amino Acid | Number of Residues | Amino Acid | Number of Residues |
| --- | --- | --- | --- | --- | --- |
| Asn | 15 | Ala | 12 | Phe | 6 |
| Thr | 6 | Val | 16 | Lys | 9 |
| Ser | 10 | Met | 1 | His | 3 |
| Gln | 20 | Ile | 5 | Arg | 3 |
| Pro | 9 | Leu | 21 | Cys | 2 |
| Gly | 10 | Tyr | 8 | Trp | 2 |
| | | | | Total | 156 |

N. Using a standard method of protein sequencing, the first 15 amino acids (N-terminal) of ATF were determined to be:

```
            5
NH2—Leu—Arg—Ser—Gln—Asn—Gln—Asn—Asp—
       10                    15
  —Lys—Asp—Lys—Ala—Val—Ala—Val—.
```

The invention will now be explained in more detail using concrete examples.

EXPERIMENT 1

Measuring method of cytotoxic activity

The activity unit of ATF was measured using mouse tumor L cells as target cells. Namely, L cells were suspended at a concentration of $2 \times 10^5$ cells/ml of Eagle's minimum essential medium (MEM) supplemented with 10% fetal calf serum (FCS, heat-inactivated) and 0.1 ml of this suspension was added to each well of a 96-well microplate and the cells were cultured at 37° C. in a 5% $CO_2$ incubator. After incubation for 24 hours, the medium was removed and exchanged for a medium containing serial four-fold dilution of ATF, and the cells were further cultured for 48 hours. The number of living cells was measured by a hemocytometer after staining with eythrosin. The titer was calculated from the reciprocal of the dilutions of ATF having 50% killing as compared to a control.

EXPERIMENT 2

In vitro cytotoxic activity of ATF on tumor cells and normal cells was measured using the medium of Example 1. The magnification of dilution corresponding to 50% killing on human lung squamous cell carcinoma (EAC-1) and human skin squamous cells carcinoma (HSC-1) was 100 and 32 fold, respectively.

On the other hand, cell killing of normal human diploid fibroblast (IMR-90) cells and Chinese hamster Don cells, was not observed, even when they were treated with the undiluted medium.

EXPERIMENT 3

The pyrogenic action of ATF

For the purpose of comparing with interleukin-1, the medium (10 ml) in Example 1 A was injected into the vein of a New Zealand white rabbit and the body temperature of the rectum was measured. As a result, the temperature rise was found to be only 0.3° C. at 1 hour after injection and 0.1° C. at 2 hours. Therefore, the substance of the invention (ATF) has no pyrogenic action.

EXPERIMENT 4

In vivo anti-tumor activity of ATF $10^6$ cells of Meth-A fibrosarcoma were transplanted under the skin at the inguinal position of BALB/c inbred mice. After 7 days, the mice were injected intraveneously with 0.2 ml (specific activity, 90 units/mg protein) of the sample which had been prepared by concentrating the medium obtained from Example 1 A.

Figure 1:
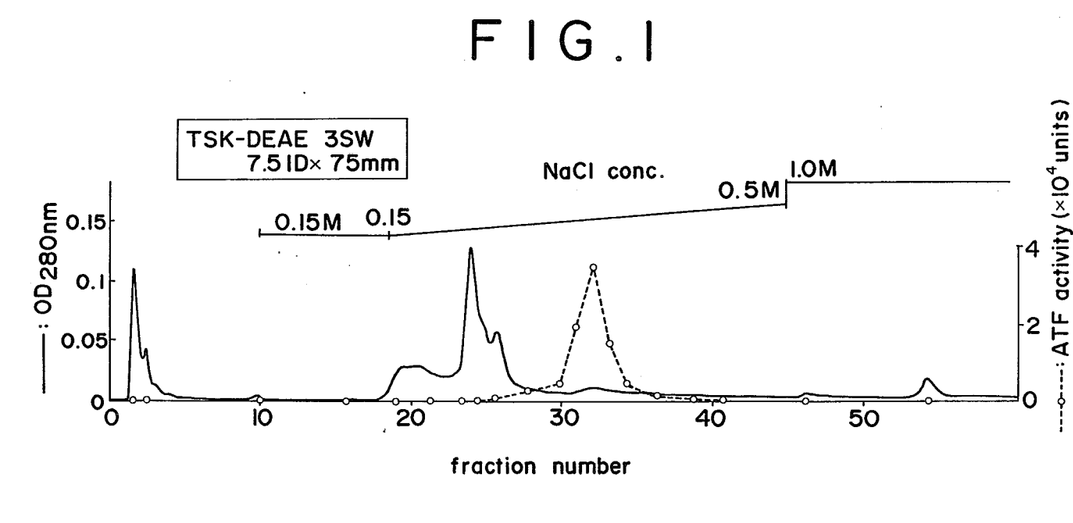
FIG. 1 shows the elution profile of ATF by HPLC with TSK-DEAE 3SW column. The ATF fraction on a TSK-G3000SW column in Experiment 5 was purified by a TSK-DEAE 3SW column. 1.2 ml fractions were collected at a flow rate of 0.6 ml/min.
Figure 2:
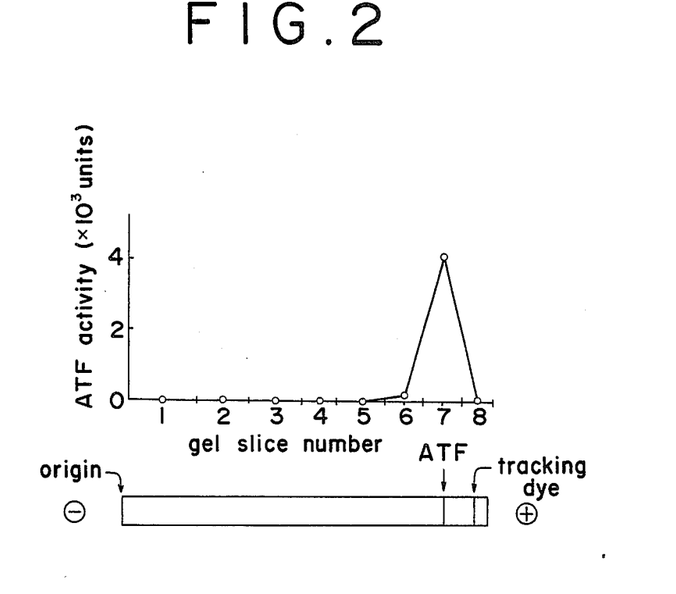
FIG. 2 shows the polyacrylamide gel electrophoretic profiles of purified ATF. The gel was stained by Coomassie Brilliant Blue. Other gels were cut at intervals of 5 mm, extracted with RPMI-1640 medium, and ATF activity was assayed.
Figure 3:
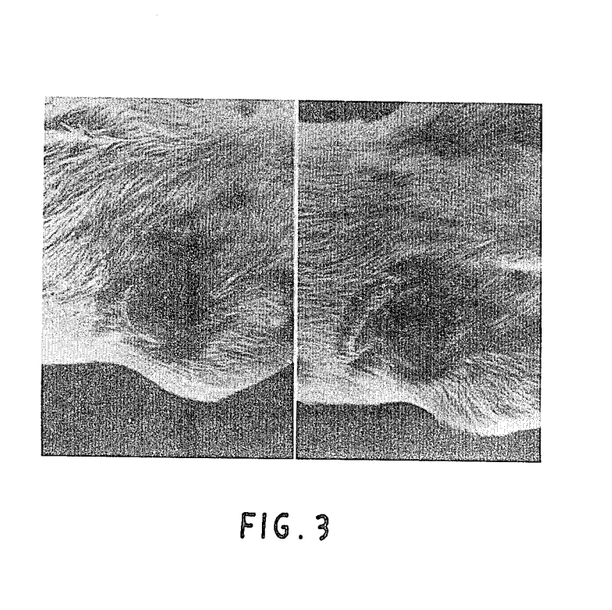
FIG. 3 shows hemorrhagic necrosis of the mouse shown in Experiment 4. The left is a control animal and the right shows the hemorrhagic necrosis at 24 hours after injection with the supernatant in Example 1A.

The day after the injection, hemorrhagic necrosis having a diameter of 2 to 3 mm was observed for 17 out of 19 mice (89%) as shown in FIG. 3.

The tumor portion of one of them was excised in order to investigate the histopathological change of the periphery of tumor tissue of the tumor.

Figure 4:
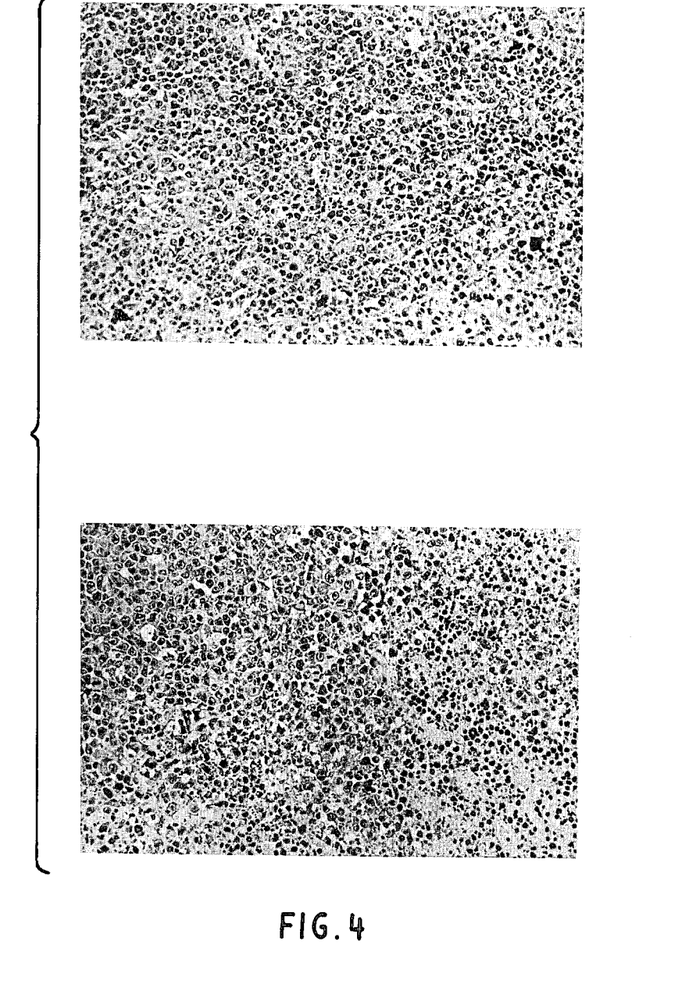
FIG. 4 is the histological preparation of Meth-A tumor tissue in Experiment 4. The upper is that of Meth-A tumor of control mice. The lower is that of the animal in which the supernatant obtained from Example 1 A was injected. In the lower, it is seen that the lymphocyte-like cells are infiltrating around the tumor cells, showing the destruction of cells.
Figure 5:
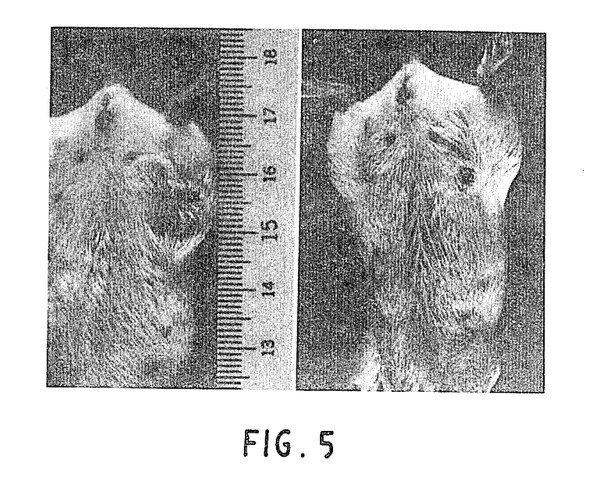
FIG. 5 shows an example of a complete cure shown in Experiment 4. The left is a control animal and the right is a mouse injected with the supernatant liquid in Example 1A.

Many lymphocyte-like cells which are suspected of originating from the host were recognized in the periphery of the tumor tissue, as shown in FIG. 4. Thereafter, the size of Meth-A sarcoma decreased with increased time of breeding. The individual tumor necrosis was remarkable. On the seventh day after injection, the formation of a crust behind the degraded tumor was observed. On the tenth day, the crust peeled off, as shown in FIG. 5. A complete disappearance of the tumor was observed in 16 out of 19 mice (84%). Although Meth-A cells were transplanted again under the skin of the completely healed individuals, they did not survive. This result indicates the existence of an acquired immunity.

EXPERIMENT 5

Effect of ammonium sulfate on the purification of ATF

Both the supernatant liquid of Example 2 and the 0–65% saturated ammonium sulfate fraction described in Example 5 were applied to a Sephacryl S-200 (Pharmacia Fine Chem.) column ($2.5 \times 85$ cm) and the difference in the molecular weight was investigated for both samples. 0.02M phosphate buffer containing 0.03M sodium chloride (ph 7.5) was used to equilibrate the column and to elute ATF. A difference in elution volume was hardly seen for the two samples.

From this result, it is considered that fractionation with ammonium sulfate did not induce association or binding with other proteins.

EXPERIMENT 6

Determination of the molecular weight of ATF

Partially purified ATF was applied to a Sephacryl S-200 (Pharmacia Fine Chem.) column ($2.5 \times 85$ cm) equilibrated with 0.02M phosphate buffer containing 0.3M sodium chloride (pH 7.5). The molecular weight of ATF was determined from the elution volume of ATF fractions having L cell killing activity. The column was calibrated with ribonuclease A, chymotrypsinogen A, ovalbumin, bovine serum albumin, and blue dextran as M.W. markers. As a result, the molecular weight was found to be $45,000 \pm 5,000$.

EXPERIMENT 7

Determination of the isoelectric point of ATF

The isoelectric point was measured by polyacrylamide disc gel electrophoresis using Ampholine (LKB Co.) as the reagent (pH range 3.5–7.0). The gel was cut at intervals of 5 mm, extracted with distilled water, and the L cell killing activity and pH of each extracted fraction was measured.

As a result, the isoelectric point of ATF was found to be pI $4.8 \pm 0.3$.

EXAMPLE 1

(A) ATF production by complete growth medium $3 \times 10^6$ cells of J774.1 were inoculated in a RPMI-1640 medium supplemented with 20% fetal calf serum (FCS), and cultured at 37° C. in a 5% $CO_2$ incubator. Many cells took the form of a sphere or monolayer, firmly adhered to the bottom of the dish, and proliferated vigorously.

When floating cells begin to appear, J774.1 cells were plated to new dishes at a dilution of 10:1 after harvesting with a rubber-policeman from confluent cultures. During this time, cultured supernatant was collected every 3 to 4 days, and the supernatant liquid containing the substance of the invention was obtained. By this method, the supernatant liquid having a titer of 500 units/ml was obtained.

(B) The L cell-killing ability (titer) increased with increasing plate number of cells or culture day. When J774.1 cells were cultured at a density of $1.4 \times 10^4$ cells/cm$^2$ in the same medium as in Example 1, the titer increased to 140 units/ml in 3 days and to 630 units/ml in 6 days. Also, at a density of $10.7 \times 10^4$ cells/cm$^2$, the titer increased to 630 units/ml on the next day and to 1,580 units/ml in 4 days.

EXAMPLE 2

ATF production by serum-free medium

After J774.1 cells were grown confluently in RPMI-1640 medium containing fetal calf serum as in Example 1, the culture medium was exchanged for serum-free medium and then J7784.1 cells were further cultured for several days. As a result, the supernatant liquid having a titer of 2,000 units/ml was obtained.

EXAMPLE 3

ATF production by roller culture method

J774.1 cells were cultured at 37° C. in a serum-free medium for 3 to 7 days by using a roller culture bottle, and a supernatant liquid containing a titer of 1,412 units/ml was obtained.

EXAMPLE 4

Mass culture by microcarrier

J774.1 cells and a microcarrier such as DEAE-dextran beads (Dainihon Seiyaku) or Cytodex (made by Pharmacia Co.) were added in a spinner flask containing RPMI-1640 medium supplement with 20% FCS. Culture was carried out for 3 days at 37° C. to allow the J774.1 cells to attach to the microcarrier. After the culture medium was exchanged (the medium containing serum for the serum-free medium), the culture was further continued at 37° C. By this method, a supernatant liquid containing 700 units/ml was obtained.

EXAMPLE 5

Purification from serum-free medium 70 ml of 0.2M phosphate buffer containing 1M sodium chloride (pH 7.5) was added to 3 liters of the supernatant obtained in Example 2. The mixture was stirred in ice, and pulverized ammonium sulfate was added to produce a 65% saturated mixture.

After 4 hours, the mixture was centrifuged (12,000 r.p.m., 30 minutes), and the precipitate was dissolved in 1.5 ml of 0.2M phosphate buffer containing 1M sodium chloride (pH 7.5). At this step, the recovery of activity was 95% and the degree of purification was 2.2 times the supernatant of the culture.

Then, the ammonium sulfate fraction was applied to a Sephacryl S-200 column (2.5 × 85 cm) which had been equilibrated previously with 0.02M phosphate buffer containing 0.1M sodium chloride (pH 7.5).

Elution was performed with the same buffer at a flow rate of 20 ml/hr. 9.7 ml fractions were collected continuously. Fractions with ATF activity were pooled and concentrated by ultrafiltration.

At this step, recovery of the activity was 99% and the degree of purification was 3.2 fold. Over all steps, the recovery of activity was 94% and the degree of purification was 7.2 fold.

Next, the active fraction obtained by gel filtration was passed through a Blue-Separose CL-6B (Pharmacia Fine Chem.) column (2.0 × 11 cm) which had been equilibrated previously with 0.01M phosphate buffer containing 0.05M sodium chloride (pH 7.5).

The flow rate was 4 ml/hr and 6 ml fractions were collected. After being washed sufficiently with the same buffer, the absorbed substance was eluted with 0.01M phosphate buffer containing 1.0M sodium chloride (pH 7.5). The absorbed fraction did not have ATF activity, and all of the activity was recovered in the non-adsorbed fraction. The active fraction was concentrated by ultrafiltration.

At this step, recovery of the activity was 84% and the degree of purification was 12 fold. Over all steps, recovery of the activity was 78% and the degree of purification was 85 fold.

Next, the active fraction was loaded onto a DEAE-Sephadex A-50 (Pharmacia Fine Chem.) column (2.0 × 8.0 cm) which had been equilibrated previously with 0.02M phosphate buffer containing 0.1M sodium chloride (pH 7.5). After washing with the same buffer, elution was conducted with 0.02M phosphate buffer containing 0.3M sodium chloride and 0.5M sodium chloride buffer, respectively.

The active fraction was eluted with 0.02M phosphate buffer containing 0.3M sodium chloride. The active fraction was concentrated by ultrafiltration.

After these steps, recovery of the activity was 80% and the degree of purification was 5 fold. Over all steps, recovery of the activity was 63% and the degree of purification was 427 fold.

The active fraction was loaded onto HPLC with TSK-G3000 SWG (2.1 ID × 60 cm TOYOSODA CO., LTD.) which had been equilibrated with 0.01M phosphate buffer containing 0.3M sodium sulfate, pH 6.8. ATF activity was eluted with the same buffer. 2 milliliter fractions were collected at a flow rate of 2.0 ml/min.

After these steps, recovery of the activity was 37% and the degree of purification was 2.4 fold. Over all steps, recovery of the activity was 23% and the degree of purification was 1025 fold.

The active fraction of TSK-G3000 SWG was loaded onto HFLC with TSK-DEAE-3WS (7.5 ID × 75 mm TOYOSODA CO., LTD) which had been equilibrated wit 0.04M phosphate buffer, pH 6.8. The column was washed with the same buffer and a buffer containing 0.15M sodium chloride, respectively. A linear salt gradient from 0.15M to 0.5M sodium chloride was used to elute ATF activity. 1.2 milliliter fractions were collected at a flow rate of 0.6 ml/min. This purified ATF showed a single band on polyacrylamide slab gel electrophoresis.

At this stage, recovery of the activity was 30% and the degree of purification was 2.5 fold. Over all steps, recovery of the activity was 7% and the degree of purification was 2,563 fold. The specific activity was $1.1 \times 10^6$ units/mg protein.

EXAMPLE 6

Purification from serum-containing medium 250 ml of 0.2M phosphate buffer containing 1M sodium chloride (pH 7.5) was added to 3 liters of supernatants obtained in Example 1. Pulverized ammonium sulfate was gradually added to the mixture under stirring in ice in order to produce a 30% saturated solution. After 3 hours, the mixture was centrifuged at 12,000 r.p.m. for 30 minutes and the supernatant was collected.

Then, the pulverized ammonium sulfate was gradually added to the supernatant under stirring in ice to produce a 65% saturated solution. After 4 hours, the mixture was centrifuged at 12,000 r.p.m. flor 30 minutes, and the precipitate was dissolved in small amounts of 0.02M phosphate buffer containing 0.1M sodium chloride (pH 7.5).

At this step, recovery of the activity was 98% and the degree of purification was 1.6 times that of the supernatant of the culture.

Then, this 30–65% fraction was dialyzed overnight with 0.02M phosphate buffer containing 0.1M sodium chloride (pH 7.5) and loaded into a DEAE-Sephadex A-50 column (9×15 cm) which had been equilibrated previously with the same buffer. After washing with the same buffer, elution was conducted with 0.02M phosphate buffer containing respective concentrations of 0.2M, 0.3M and 0.5M sodium chloride (pH 7.5). The fractionation was conducted each 15 ml at a flow rate of 60 ml/hr and the active fractions were concentrated by ultrafiltration.

At this step, the recovery of the activity was 93% and the degree of the purification was 38 fold. Over all steps, the recovery of the activity was 72% and the degree of the purification was 60 fold.

Next, the active fraction obtained above was applied to a Sephacryl S-200 column (2.5×85 cm) which had been equilibrated previously with 0.02M phosphate buffer containing 0.1M sodium chloride (pH 7.5). The fractionation was conducted each 6 ml at a flow rate of 20 ml/hr.

At this step, recovery of the activity was 95% and the degree of purification was 12 fold. Over all steps, recovery of the activity was 68% and the degree of purification was 725 fold.

Next, the active fraction was concentrated by ultrafiltration and passed through a Blue-Sepharose CL-6B column (5×10 cm) which had been equilibrated previously with 0.01M phosphate buffer containing 0.05M sodium chloride (pH 7.5). The absorbed fraction was eluted with 0.01M phosphate buffer solution containing 1.0M sodium chloride (pH 7.5). The activity was observed in the non-absorbed fraction. The active fraction was concentrated.

At this step, recovery of the activity was 82% and the degree of purification was 6 fold. Over all steps, the recovery of the activity was 56% and the degree of purification was 4,320 fold.

The active fraction was loaded onto HPLC with TSK-G3000SWG (2.1ID×60 cm TOYOSODA CO., LTD.) which had been equilibrated with 0.01M phosphate buffer containing 0.3M sodium sulfate, pH 6.8. ATF activity was eluted with the same buffer. 2 milliliter fractions were collected at a flow rate of 2.0 ml/min.

At this step, recovery of the activity was 35% and degree of purification was 4 fold. Over all steps, recovery of the activity was 20% and the degree of purification was 17,280 fold. The active fraction of TSK-G3000SWG was loaded onto HPLC with TSK-DEAE-3SW (7.5ID×75 mm TOYOSODA CO., LTD.) which had been equilibrated with 0.04M phosphate buffer pH 6.8. The column was washed with the same buffer and a buffer containing 0.15M sodium chloride, respectively. A linear salt gradient from 0.15M to 0.5M sodium chloride was used to elute ATF activity. 1.2 milliliter fractions were collected at a flow rate of 0.6 ml/min. This purified ATF showed a single band on polyacrylamide slab gel electrophoresis.

At this step, recovery of the activity was 28% and the degree of purification was 3 fold.

Over all steps, recovery of the activity was 6% and the degree of purification was 51,840 fold. The specific activity was $1.0 \times 10^6$ units/mg protein.

EXAMPLE 7

Purification of ATF with a monoclonal antibody

1. Production of monoclonal hybridoma

Partially purified ATF is injected subcutaneously into C3H/HeN mice (other species may be used, if necessary) together with an adjuvant. Afterwards, immunization once a week was carried out 3 to 4 times. Mice showing a high titer of ATF are injected intraperitoneally without adjuvant, and 3 days later, the mice are killed and their spleens are removed. To prepare the spleen cells, the spleen is minced by pincettes and the erythrocytes are removed with hemolysis buffer. The spleen cells are mixed with mouse myeloma cells (P3-x 63-Ag 8.653 or P3 NS-1) at a ratio of 10:1 to 1:1. Both kinds of cells are fused with polyethylene glycol. The fused cells are cultured in HAT selection medium for about 2 weeks, and they are further cultured in HAT medium removing aminopterin from the HAT medium.

The supernatant of the cultured fused cells and appropriately diluted ATF solution are added to the L cell culture at the same time.

The fused cells having an ability to neutralize the activity of ATF are selected, these cells being presumed to be hybridomas producing antibodies against ATF. Cloning of the hybridomas is carried out by the limiting dilution method. The cloning cells are again submitted to screening at a time when the cells have proliferated to an appropriate number, and the positive ones are submitted to cloning again.

2. Mass production of the monoclonal antibody and purification

First, the clone which has the highest activity among the established hybridoma clones producing anti-ATF antibody is selected. The clone is cultured on a large scale to produce a large amount of the antibody. There are two methods of large scale culture. One is a method in which 10 cells are intraperitoneally injected into mice, and allowed to proliferate as an ascites cancer, and the other is a method in which the cells are cultured in a large flask using serum-free medium. After concentrating the ascites or the supernatant liquid of the culture by using ammonium sulfate or ultrafiltration, the immunoglobulin is removed by passage through an ion-exchange resin such as DEAE-Sephadex, etc. or protein A-cellulose.

3. Purification of ATF with an affinity column

Purified immunoglobulin is bonded to a carrier such as Agarose or Sepharose activated with CNBr, and a column having an appropriate volume is filled with the bonded carrier. After allowing only ATF to bind, by passing the culture supernatant liquid of the massive culture of J774.1 cells through this column, ATF is eluted by raising the ionic strength to obtain pure ATF.

4. Determination with labelled antibody

By labelling the obtained monoclonal antibody with $^{125}I$, the content of ATF can be determined more rapidly than by measurement of activity by the biological method.

What is claimed is:

1. A proteinaceous substance having the following biochemical characteristics:
   (A) said substance has a high tumor specificity as evidenced by its strong cytolytic activity against mouse tumor cells L-929 and L-1210, and human carcinoma HeLa cells, and lack of cytotoxic activity against normal human fetus fibroblasts, normal human adult skin fibroblasts or normal Chinese hamster fibroblasts (Don, V-79);
   (B) said substance has a strong anti-tumor activity against Meth-A sarcoma, as evidenced by the fact that when said substance is administered intravenously to syngeneic BALB/c mice inoculated with Meth-A sarcoma at a quantity of more than 72 units/head, hemorrhagic necrosis of the tumor is observed, and subsequent successful implantation of Meth-A sarcoma cells in the same mice is not observed because of acquired immunity;
   (C) said substance has no pyrogenic effect on rabbits after intravenous injection;
   (D) said substance has a molecular weight of 45,000 plus or minus 5,000 as determined by gel filtration with Sepharcryl S-200;
   (E) said substance has an isoelectric point of 4.8 plus or minus 0.3;
   (F) said substance is sensitive to tyrpsin, but stable to heating at 56° C. for 30 minutes;
   (G) said substance is not glycosylated; and
   (H) said substance contains the following first 15 N-terminal amino acids:

$$NH_2-Leu-Arg-Ser-Gln-Asn-Gln-Asn-Asp-$$
$$-Lys-Asp-Lys-Ala-Val-Ala-Val-$$

(I) said substance contains the following amino acid content:

TABLE

| Amino Acid | Number of Residues | Amino Acid | Number of Residues | Amino Acid | Number of Residues |
|---|---|---|---|---|---|
| Asn | 15 | Ala | 12 | Phe | 6 |
| Thr | 6 | Val | 16 | Lys | 9 |
| Ser | 10 | Met | 1 | His | 3 |
| Gln | 20 | Ile | 5 | Arg | 3 |
| Pro | 9 | Leu | 21 | Cys | 2 |
| Gly | 10 | Tyr | 8 | Trp | 2 |
|  |  |  |  | Total | 156 |

2. The substance of claim 1, wherein said substance is obtained by allowing cultured mammalian tumor cells to proliferate in complete growth medium containing calf fetal serum, wherein said tumor cells are histocytes showing phagocytic activity, followed by culturing said cells in a serum-free medium in order to obtain a supernatant liquid of the culture containing said proteinaceous substance, and isolating said substance.

3. The proteinaceous substance of claim 2, which is derived from histocyte-type J-774.1 reticulosarcoma cultured cells having phagocytic activity.

4. The proteinaceous substance of claim 2, which is derived from cloned culture cells derived from human lymph nodes, wherein said cultured cells are selected from the group consisting of U-937, RS-3, MC-8-3, MKC-12, RPMI-8866, ARH-77, WA and KCCL cells, wherein said cells are histocyte-type cells having a round shape and phagocytic activity.

5. The proteinaceous substance of claim 2, which is derived from cloned cultured cells which are tumor cells of human myeloma selected from the group consisting of K-562, D-98 and OST cells, and wherein said cultured cells have a round shape and phagocytic activity.

6. The proteinaceous substance according to claim 2, which is derived from a human Burkitt lymphoma selected from the group consisting of EB-3, Raji, and P3HR-1, wherein said cultured cells are histocyte-type cells having phagocytic activity.

7. The proteinaceous substance according to claim 2, wherein said substance is derived from hybridoma cells, wherein said hybridoma cells are fused U-937 cells and human B cells.

8. The proteinaceous substance of claim 7, wherein said human B cells are BALL-1 cells.

9. The proteinaceous substance according to claim 2, which is derived from mouse lymphoma cells selected from the group consisting of RAW-264, IC-21, P388D1 and PU5-1.8 cells, wherein said cells have phagocytic activity.

10. The proteinaceous substance of claim 2, wherein said substance is produced by adding a trace of 2-mercaptoethanol or a trace of phorbol myristate acetate to a series of said cultured cells.

11. A method for obtaining a substantially purified proteinaceous substance according to claim 2, wherein after the supernatant liquid cultured in the serum-free medium is precipitated with ammonium sulfate and is added to a gel filtrating column with Sephacryl S-200, the portion not absorbed with blue Separose is collected and passed through DEAE-Sephadex A-50.

* * * * *